United States Patent [19]

Cantatore et al.

[11] Patent Number: 4,927,930

[45] Date of Patent: May 22, 1990

[54] POLYAMINES PARTIALLY SUBSTITUTED BY PIPERIDINE-TRIAZINES

[75] Inventors: Giuseppe Cantatore, Bitonto; Valerio Borzatta, Bologna; Franca Masina, Anzola Emilia, all of Italy

[73] Assignee: Ciba-Geigy Corporation, Ardsley, N.Y.

[21] Appl. No.: 356,814

[22] Filed: May 24, 1989

[30] Foreign Application Priority Data

May 31, 1988 [IT] Italy ................................ 20809 A/88

[51] Int. Cl.$^5$ ...................... C07D 251/40; C08J 5/34; C09K 15/16
[52] U.S. Cl. ...................... 544/198; 544/113; 544/209; 540/598; 252/401; 252/402; 252/403; 524/83; 524/100
[58] Field of Search ...................... 544/198, 209, 113; 540/598

[56] References Cited

U.S. PATENT DOCUMENTS

| 4,108,829 | 8/1978 | Cassandrini et al. ................ 544/198 |
| 4,288,593 | 9/1981 | Rody ..................................... 544/198 |

FOREIGN PATENT DOCUMENTS

| 904401 | 6/1986 | Belgium ............................. 544/198 |
| 0299925 | 1/1989 | European Pat. Off. . |
| 2120248 | 11/1983 | United Kingdom ................ 544/198 |
| 2194237 | 3/1988 | United Kingdom ................ 544/198 |

OTHER PUBLICATIONS

Chem. Abst. 105, 209942q (1986) of Belgian 904,401.

*Primary Examiner*—Mary C. Lee
*Assistant Examiner*—J. Richter
*Attorney, Agent, or Firm*—Luther A. R. Hall

[57] ABSTRACT

The present invention relates to novel piperidyl-triazine compounds with 2 or more triazine rings, to their use as light stabilizers, heat stabilizers and oxidation stabilizers for organic materials, and to the organic materials thus stabilized.

10 Claims, No Drawings

POLYAMINES PARTIALLY SUBSTITUTED BY PIPERIDINE-TRIAZINES

It is known that synthetic polymers undergo a progressive change in mechanical strength and variation in colour when they are exposed to sunlight or other sources of ultraviolet light in the presence of oxygen.

To retard the photooxidative degradation of synthetic polymers, it has been proposed to use various additives having photostabilizing properties, such as some derivatives of benzophenone and benzotriazole, nickel complexes, substituted benzoic acid esters, alkylidene malonates, cyanoacrylates, aromatic oxamides and sterically hindered amines.

Some triazine derivatives of 2,2,6,6-tetramethyl-4-piperidylamine have shown effectiveness as light stabilizers. In particular, U.S. Pat. No. 4,108,829, U.S. Pat. No. 4,288,593 and BE No. 904,401 describe, for example, dialkylenetriamines which contain polyalkyl-4-piperidyl-triazine groups.

The present invention relates to novel piperidine-triazine compounds of the general formula (I)

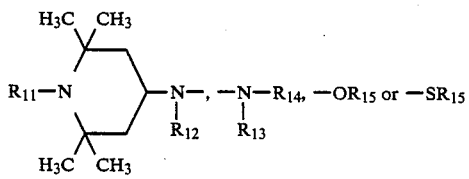

in which $R_1$ is hydrogen, $C_1$–$C_4$alkyl, O*, OH, NO, $CH_2CN$, $C_1$–$C_8$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl, $C_1$–$C_8$acyl or $C_2$–$C_4$alkyl substituted by one OH in the 2-, 3- or 4-position, $R_2$ is hydrogen, $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, or $C_2$–$C_4$alkyl substituted by OH, $C_1$–$C_8$alkoxy or di-($C_1$–$C_4$alkyl)-amino in the 2-, 3- or 4-position, $R_3$ is $C_1$–$C_{18}$alkyl, phenyl which is unsubstituted or mono-,di- or tri-substituted by $C_1$–$C_4$alkyl, or one of the groups

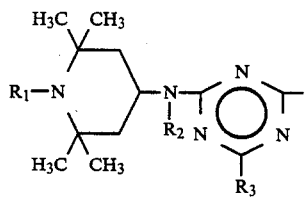

in which $R_{11}$ is as defined above for $R_1$, $R_{12}$ is as defined above for $R_2$, $R_{13}$ and $R_{14}$ which can be identical or different are as defined above for $R_2$ or are $C_3$–$C_6$alkenyl or, together with the nitrogen atom to which they are linked, form part of a 5-membered to 7-membered heterocyclic ring and $R_{15}$ is $C_1$–$C_{18}$alkyl, $C_5$–$C_{12}$cycloalkyl which is unsubstituted or mono-, di- or tri-substituted by $C_1$–$C_4$alkyl, $C_3$–$C_6$alkenyl, phenyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, or a group of the formula (II)

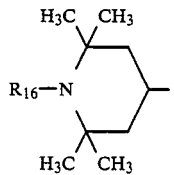

with $R_{16}$ being as defined above for $R_1$, $R_4$ and $R_{10}$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl or a group of the formula (II), $R_5$, $R_7$ and $R_9$ which can be identical or different are $C_2$–$C_{12}$alkylene, n is zero or 1, $R_6$ and $R_8$ are $C_1$–$C_{18}$alkyl, $C_5$–$C_{12}$cycloalkyl which is unsubstituted or mono-, di- or tri-substituted by $C_1$–$C_4$alkyl, $C_3$–$C_6$alkenyl, $C_7$–$C_9$phenylalkyl which is unsubstituted or mono-, di- or tri-substituted on the phenyl by $C_1$–$C_4$alkyl, $C_2$–$C_4$alkyl substituted by OH in the 2-, 3- or4-position, or a group of the formula (II) or $R_6$ and $R_8$ are one of the groups of the formula (IIIa)-(IIId)

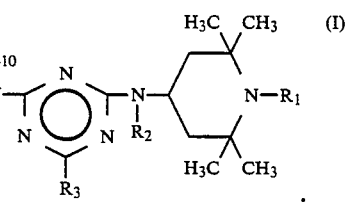

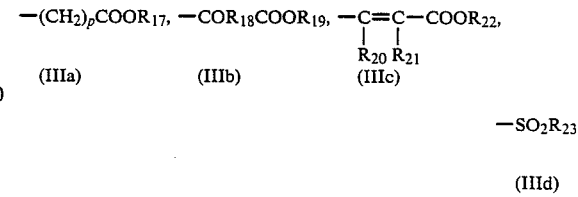

in which p is zero or an integer from 1 to 5, $R_{17}$, $R_{19}$ and $R_{22}$ which can be identical or different are $C_1$–$C_{18}$alkyl, $C_5$–$C_{12}$cycloalkyl which is unsubstituted or mono-, di- or tri-substituted by $C_1$–$C_4$alkyl, $C_3$–$C_{18}$alkenyl or a group of the formula (II), $R_{18}$ is a direct bond or $C_1$–$C_{12}$alkylene, cyclohexylene or phenylene, $R_{20}$ is hydrogen, $C_1$–$C_4$alkyl or phenyl, $R_{21}$ is —CN or a group —COOR$_{22}$ with $R_{22}$ being as defined above, and $R_{23}$ is $C_1$–$C_{18}$alkyl or phenyl which is unsubstituted or mono-, di- or tri-substituted by $C_1$–$C_4$alkyl, or $R_8$ is a group of the formula (IV)

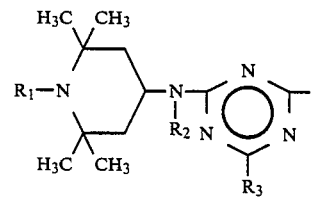

with $R_1$, $R_2$ and $R_3$ being as defined above, and, if n is zero or if $R_8$ is group of the formula (IV), $R_6$ can also be one of the groups of the formulae (Va) or (Vb)

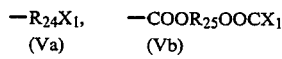

where $R_{24}$ is $C_2$-$C_{12}$alkylene, 2-hydroxytrimethylene or xylylene and $R_{25}$ is $C_2$-$C_{12}$alkylene, $C_4$-$C_{12}$alkylne interrupted by 1, 2 or 3 oxygen atoms, cyclohexylenedimethylene, methylenedicyclohexylene, isopropylidenedicyclohexylene, phenylene, xylylene or a group

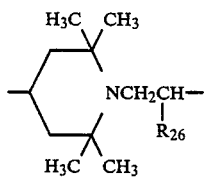

with $R_{26}$ being hydrogen, $C_1$-$C_4$alkyl or phenyl, and $X_1$ is a group of the formula (VI)

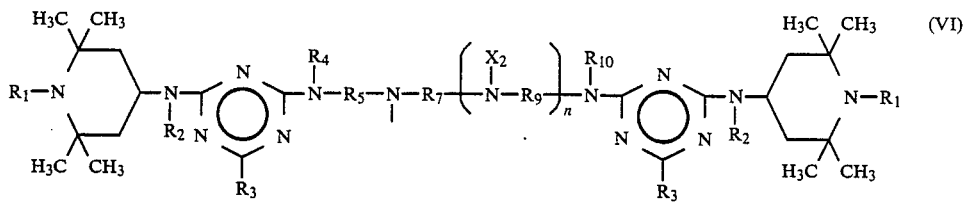

where $R_1$, $R_2$, $R_3$, $R_4$, $R_5$, $R_7$, $R_9$, $R_{10}$ and n are as defined above, and $X_2$ is a group of the formula (IV).

Representative examples of $C_1$-$C_4$alkyl $R_1$, $R_{11}$, $R_{16}$, $R_{20}$, and $R_{26}$ are methyl, ethyl, propyl, butyl and isobutyl.

$R_1$, $R_{11}$ and $R_{16}$ are preferably methyl.

Examples of $C_1$-$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$R_2$, $R_4$, $R_6$, $R_8$, $R_{10}$ and $R_{12}$ are preferably $C_1$-$C_{12}$alkyl, in particular $C_1$-$C_8$alkyl, and $R_{17}$, $R_{19}$ and $R_{22}$ are preferably $C_1$-$C_{16}$alkyl.

Examples of OH-substituted $C_2$-$C_4$alkyl are 2-hydroxyethyl, 2-hydroxypropyl, 3-hydroxypropyl, 2-hydroxybutyl and 4-hydroxybutyl. 2-Hydroxyethyl is a preferred example of $R_1$, $R_{11}$ and $R_{16}$. Examples of $C_2$-$C_4$alkyl substituted by $C_1$-$C_8$alkoxy, preferably $C_1$-$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$-$C_{18}$alkoxy $R_1$, $R_{11}$ and $R_{16}$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$alkoxy in particular heptoxy or octoxy, is preferred.

Examples of $C_5$-$C_{12}$cycloalkyl which is unsubstituted or substituted by $C_1$-$C_4$alkyl, in particular methyl, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl.

Representative examples of $C_5$-$C_{12}$cycloalkoxy $R_1$, $R_{11}$ and $R_{16}$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are allyl, 2-methylallyl, hexenyl, decenyl, undecenyl and oleyl. The carbon atom in the position 1 of the alkenyl group is preferably a primary carbon atom.

Examples of substituted phenyl are methylphenyl, dimethylphenyl, trimethylphenyl, t-butylphenyl and di-t-butylphenyl.

Examples of phenylalkyl which is unsubstituted or substituted on the phenyl, are benzyl, methylbenzyl, dimethylbenzyl, t-butylbenzyl and 2phenylethyl. Benzyl is preferred.

$C_1$-$C_8$acyl $R_1$, $R_{11}$ and $R_{16}$ can be aliphatic or aromatic acyl groups. $C_1$-$C_8$-alkanoyl, $C_3$-$C_8$alkenoyl and benzoyl are preferred. Representative examples are formyl, acetyl, propionyl, butyryl, valeryl, caproyl, capryloyl, benzoyl, acryloyl and crotonyl.

Examples of alkylene having up to 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene. Alkylene having up to 10 carbon atoms, especially up to 8 carbon atoms, is preferred. $R_5$, $R_7$ and $R_9$ are in particular $C_2$-$C_3$alkylene.

Examples of $C_4$-$C_{12}$alkylene interrupted by 1, 2 or 3 oxygen atoms are 3-oxapentane-1,5-diyl, 3,6-dioxaoctane-1,8-diyl and 3,6,9-trioxaundecane-1,11-diyl. 3-Oxapentane-1,5-diyl is preferred.

If $R_{13}$ and $R_{14}$, together with the nitrogen atom to which they are linked, form a 5-membered to 7-membered heterocyclic radical, which preferably contains a further heteroatom, for example nitrogen or oxygen, representative examples are pyrrolidyl, piperidyl, morpholinyl, N-methylpiperazinyl and hexahydroazepinyl.

Those compounds of the formula (I) are preferred in which $R_2$ is hydrogen, $C_1$-$C_{12}$alkyl, $C_5$-$C_8$cycloalkyl which is unsubstituted or mono-, di- or trisubstituted by $C_1$-$C_4$alkyl, benzyl or $C_2$-$C_3$alkyl substituted by OH $C_1$-$C_4$alkoxy or di-($C_1$-$C_4$alkyl)-amino in the 2- or 3-position, $R_3$ is $C_1$-$C_{12}$alkyl, phenyl or one of the groups

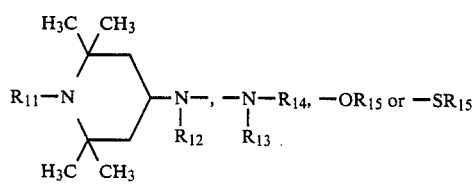

in which $R_{11}$ is as defined above, $R_{12}$ is as defined above for $R_2$, $R_{13}$ and $R_{14}$ which can be identical or different are as defined above for $R_2$ or are allyl, or the group

is 1-pyrrolidyl, 1-piperidyl, 4-morpholinyl or 1-hexahydroazepinyl and $R_{15}$ is $C_1$–$C_{12}$alkyl, $C_5$–$C_8$cycloalkyl which is unsubstituted or mono-, di- or tri-substituted by $C_1$–$C_4$alkyl, allyl, phenyl, benzyl or a group of the formula (II) with $R_{16}$ being as defined for $R_1$, $R_4$ and $R_{10}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, or a group of the formula (II), $R_5$, $R_7$ and $R_9$ which can be identical or different are $C_2$–$C_{10}$alkylene, n is zero or 1, $R_6$ and $R_8$ are $C_1$–$C_{12}$alkyl, $C_5$–$C_8$cycloalkyl which is unsubstituted or mono-, di- or tri-substituted by $C_1$–$C_4$alkyl, allyl, benzyl, $C_2$–$C_3$alkyl substituted by OH in the 2- or 3-position, or a group of the formula (II) or $R_6$ and $R_8$ are one of the groups of the formulae (IIIa)–(IIId) in which p is zero or an integer from 1 to 3, $R_{17}$, $R_{19}$ and $R_{22}$ which can be identical or different are $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (II), $R_{18}$ is a direct bond or $C_1$–$C_{10}$alkylene, $R_{20}$ is hydrogen or $C_1$–$C_4$alkyl, $R_{21}$ is —CN or a group —COOR$_{22}$ with $R_{22}$ being as defined above and $R_{23}$ is $C_1$–$C_{12}$alkyl, phenyl or tolyl, or $R_8$ is a group of the formula (IV) and $R_6$ is a group of the formula (Va) or (Vb) in which $R_{24}$ is $C_2$–$C_{10}$alkylene, 2-hydroxytrimethylene or xylylene, $R_{25}$ is $C_2$–$C_{10}$alkylene, $C_4$–$C_8$-alkylene interrupted by 1, 2 or 3 oxygen atoms, cyclohexylenedimethylene, isopropylidenedicyclohexylene or a group

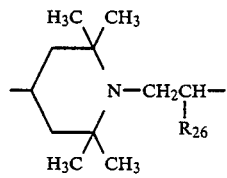

with $R_{26}$ being hydrogen or methyl, and $X_1$ is a group of the formula (VI).

Those compounds of the formula (I) are particularly preferred in which $R_2$ is hydrogen, $C_1$–$C_{12}$alkyl, cyclohexyl which is unsubstituted or mono-, di- or tri-substituted by $C_1$–$C_4$alkyl, benzyl or $C_2$–$C_3$alkyl substituted by OH, methoxy, ethoxy, dimethylamino or diethylamino in the 2-or 3-position, $R_3$ is $C_1$–$C_4$alkyl, phenyl or one of the groups

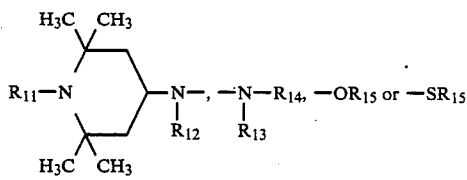

in which $R_{11}$ is as defined above, $R_{12}$ is as defined above for $R_2$, $R_{13}$ and $R_{14}$ which can be identical or different are as defined above for $R_2$ or are allyl, or the group

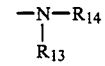

is 4-morpholinyl, and $R_{15}$ is $C_1$–$C_8$alkyl, cyclohexyl which is or mono-, di- or tri-substituted by $C_1$–$C_4$alkyl, allyl, phenyl, benzyl or a group of the formula (II) with $R_{16}$ being as defined above for $R_1$, $R_4$ and $R_{10}$ which can be identical or different are hydrogen, $C_1$–$C_8$alkyl, cyclohexyl or a group of the formula (II), $R_5$, $R_7$ and $R_9$ which can be identical or different are $C_2$–$C_8$alkylene, n is zero or 1, $R_6$ and $R_8$ are $C_1$–$C_8$alkyl, cyclohexyl which is unsubstituted or mono-, di- or tri-substituted by $C_1$–$C_4$alkyl, allyl, benzyl, 2-hydroxyethyl or one of the groups of the formulae (IIIa)–(IIId) in which p is zero or 1, $R_{17}$, $R_{19}$ and $R_{22}$ which can be identical or different are $C_1$–$C_{16}$alkyl, cyclohexyl which is unsubstituted or mono-, dior tri-substituted by $C_1$–$C_4$alkyl, allyl, oleyl or a group of the formula (II), $R_{18}$ is a direct bond or $C_1$–$C_8$alkylene, $R_{20}$ is hydrogen or methyl, $R_{21}$ is —CN or a group —COOR$_{22}$ with $R_{22}$ being as defined above, and $R_{23}$ is $C_1$–$C_8$ alkyl, phenyl or tolyl, or $R_8$ is a group of the formula (IV) and $R_6$ can also be a group of the formula (Va) or (Vb) in which $R_{24}$ is $C_2$–$C_8$-alkylene, 2-hydroxytrimethylene or xylylene, $R_{25}$ is $C_2$–$C_8$alkylene, $C_4$–$C_6$alkylene interrupted by 1 or 2 oxygen atoms, cyclohexylenedimethylene, isopropylidenedicyclohexylene or a group

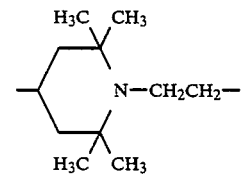

and $X_1$ is a group of the formula (VI).

Compounds of the formula (I) of special interest are those in which $R_2$ is hydrogen, $C_1$–$C_8$alkyl, cyclohexyl or $C_2$–$C_3$alkyl, which is substituted by OH, methoxy or ethoxy in the 2- or 3-position, $R_3$ is a group

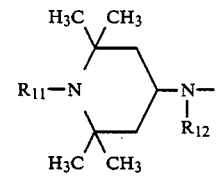

with $R_{11}$ being as defined above and $R_{12}$ being as defined above for $R_2$, $R_4$ and $R_{10}$ which can be identical or different are hydrogen, $C_1$–$C_4$alkyl, cyclohexyl or a group of formula (II), $R_5$, $R_7$ and $R_9$ which can be identical or different are $C_2$–$C_6$alkylene, n is zero or 1, $R_6$ and $R_8$ are $C_1$–$C_4$alkyl, allyl, benzyl or one of the groups of the formulae (IIIa)(IIIc) in which p is zero, $R_{17}$, $R_{19}$ and $R_{22}$ which can be identical or different are $C_1$–$C_{12}$alkyl, cyclohexyl, t-butylcyclohexyl or a group of the formula (II), $R_{18}$ is a direct bond, $R_{20}$ is hydrogen and $R_{21}$ is —CN, or $R_8$ is a group of the formula (IV) and $R_6$ is also a group of the formula (Vb) in which $R_{25}$ is $C_4$–$C_8$alkylene, 3-oxapentane-1,5-diyl, cyclohexylenedimethylene or isopropylidenedicyclohexylene and $X_1$ is a group of the formula (VI).

Compounds of the formula (I) of particular interest are those in which $R_1$ is hydrogen or methyl, $R_2$ is $C_1$–$C_8$alkyl, $R_3$ is a group

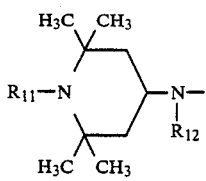

with $R_{11}$ being hydrogen or methyl and $R_{12}$ being $C_1$–$C_8$alkyl, $R_4$ and $R_{10}$ which can be identical or different are hydrogen or methyl, $R_5$, $R_7$ and $R_9$ which can be identical or different are —$(CH_2)_{2-3}$—, $n$ is zero or 1, $R_6$ and $R_8$ are methyl or a group —$COOR_{17}$ or

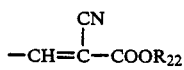

where $R_{17}$ and $R_{22}$ which can be identical or different are $C_1$–$C_8$alkyl, 2,2,6,6-tetramethyl-4-piperidyl or 1,2,2,6,6-pentamethyl-4-piperidyl, or $R_8$ is a group of the formula (IV) and $R_6$ is also a group —$COO(CH_2)_{4-6}OOCX_1$, where $X_1$ is a group of the formula (VI).

$R_1$, $R_{11}$ and $R_{16}$ independently of one another are preferably hydrogen, $C_1$–$C_4$alkyl, OH, $C_6$–$C_{12}$alkoxy, $C_5$–$C_8$cycloalkoxy, allyl, benzyl, acetyl or 2-hydroxyethyl, in particular hydrogen or methyl.

Those compounds of the formula (I) are also of interest in which $R_3$ is a group of the formula

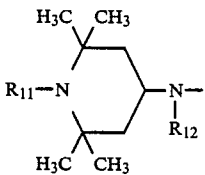

where $R_{11}$ and $R_{12}$ are as defined above, $R_4$ and $R_{10}$ independently of one another are hydrogen, $C_1$–$C_4$alkyl or a group of the formula (II), $R_6$ and $R_8$ independently of one another are $C_1$–$C_4$alkyl or a group of the formula (IIIa) or (IIIc), $R_8$ is additionally a group of the formula (IV) and $R_6$ is additionally a group of the formula (Vb).

$R_3$ is preferably a group of the formula

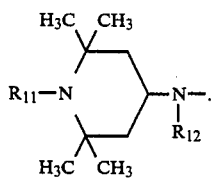

The compounds of the formula (I) can be prepared by processes known per se, for example by reacting a chlorotriazine of the formula (VII)

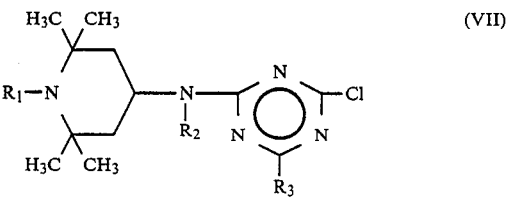

with $R_1$, $R_2$ and $R_3$ being as defined above, with a polyamine of the formula (VIII)

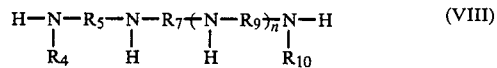

with $R_4R_5$, $R_7$, $R_9$, $R_{10}$ and being as defined above, by operating as described, for example, in U.S. Pat. No. 4,108,829, the molar ratio of compound of the formula (VII):compound of the formula (VIII) being e.g. equal to 2:1 if n is zero, and e.g. 2:1 to 3:1 if n is 1.

Compounds of the formula (I) can be obtained in this way, in which $R_6$ is hydrogen and $R_8$ is hydrogen or a group of the formula (IV); from these compounds, the corresponding compounds with $R_6$ and $R_8$ other than H can be obtained e.g. successively by reaction with suitable alkylating or acylating reagents.

If $R_6$ and $R_8$ are $C_1$–$C_{18}$alkyl, $C_5$–$C_{12}$cycloalkyl, $C_7$–$C_9$phenylalkyl or a group of the formula (II), the compounds of the formula (I) can be obtained directly, for example by reacting a chlorotriazine of the formula (VII) with a polyamine of the formula (IX)

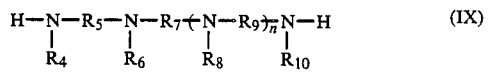

in which $R_4$, $R_5$, $R_7$, $R_9$, $R_{10}$ and n are as defined before and $R_6$ and $R_8$ are as defined above.

If $R_6$ and $R_8$ are methyl, the compounds of the formula (I) are preferably prepared by reacting the corresponding unsubstituted compounds with formaldehyde and formic acid (Eschweiler-Clarke reaction) or with formaldehyde and hydrogen in the presence of a hydrogenation catalyst such as e.g. palladium or platinum.

In these reactions, the piperidine >NH groups can also be methylated and, under suitable conditions, also the melamine >NH groups which may be present.

The reactions of the chlorotriazines of the formula (VII) with the polyamines of the formula (VIII) or (IX) are preferably carried out in an aromatic hydrocarbon solvent, for example toluene, xylene, ethylbenzene or trimethylbenzene, operating at a temperature from e.g. −20° to 200° C., preferably from −10° to 180° C. The successive substitution reactions are preferably carried out by directly using the reaction mixture obtained in the first stage, but it is also possible to separate the intermediate compounds with $R_6$ and possibly $R_8$ being H, and using them in the successive alkylation or acylation reactions followed ultimately by possible purification using, if appropriate, a solvent other than that employed in the first stage.

The hydraulic acid eliminated in the various reactions is conveniently neutralized with an inorganic base, for example sodium or potassium hydroxide or carbonate, in a quantity at least equivalent to the acid eliminated.

The product obtained can optionally be a mixture of possible isomers which are obtainable in the partial substitution reaction of the polyamines of the formula (VIII) with the chlorotriazines of the formula (VII).

As mentioned at the outset, the compounds of the formula (I) are highly effective in improving the light stability, heat stability and oxidation stability of organic materials, in particular synthetic polymers and copolymers. The very high stabilizing activity of the compounds of the invention against oxidation is particularly surprising. The invention therefore also relates to a composition containing an organic material, which is susceptible to thermal, oxidative or light-induced degradation, and at least one compound of the formula (I).

Examples of organic materials are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in (1) above, for example polypropylene/ethylene-propylene copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-($\alpha$-methylstyrene).

5. Copolymers of styrene or $\alpha$-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or $\alpha$-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS, MBS, ASA or AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, 6/9, 6/12 and 4/6, polyamide 11, polyamide 12, aromatic polyamides obtained by condensation of m-xylylenediamine and adipic acid; polyamides prepared from hexamethylenediamine and isophthalic or/and terephthalic acid and optionally an elastomer as modifier, for example poly-2,4,4-trimethylhexamethylene-terephthalamide or poly-m-phenyleneisophthalamide. Further, copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane]terephthalate and polyhydroxybenzoates as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine formaldehyde resins.

21. Drying and non-drying alkyl resins.

22. Unsaturated polyester resins which are derived from copolyesters of saturated and unsaturated dicarboxylic acids with polyhydric alcohols and vinyl compounds as crossslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in a mixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and soaps based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

Compounds of the formula (I) are particularly suitable for improving the light stability, heat stability and oxidation stability of polyolefins, especially polyethylene and polypropylene.

The compounds of the formula (I) can be used in mixtures with organic materials, including synthetic polymers, in various proportions depending on the nature of the material to be stabilized, on the end use and on the presence of other additives.

In general, it is appropriate to use, for example, 0.01 to 5% by weight of the compounds of the formula (I) relative to the weight of the materials to be stabilized, preferably from 0.05 to 1%.

The compounds of the formula (I) can be incorporated in the polymeric materials by various processes, such as dry mixing in the form of powder, or wet mixing in the form of solutions or suspensions or also in the form of a master batch; in such operations, the polymer can be used in the form of powder, granules, solutions, suspensions or in the form of lattices.

The polymers stabilized with the products of the formula (I) can be used for the production of mouldings, films, tapes, monofilaments, surface coatings and the like.

If desired, other conventional additives for synthetic polymers, such as antioxidants, UV absorbers, nickel stabilizers, pigments, fillers, plasticizers, antistatic agents, flameproofing agents, lubricating agents, corrosion inhibitors and metal deactivators, can be added to the mixtures of the compounds of the formula (I) with the organic materials.

Particular examples of additives which can be used in a mixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tertbutyl-4methylphenol), 2,2'-methylenebis(6-tert-butyl-4-ethylphenol), 2,2'-methylenebis[4-methyl-6-( -methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-$\alpha$-methylbenzyl)-4-nonylphenol], 2,2'-methylenebis[6-($\alpha,\alpha$-dimethylbenzyl)-4-nonylphenol], 4,4'-methylenebis((2,6-di-tertbutylphenol), 4,4'-methylenebis(6-tert-butyl-2-methylphenol), 1,1-bis(5-methyltertbutyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tertbutyl-4-hydroxy-5-methylphenyl)dicyclopentadiene, bis[2-(3'-tertbutyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4hydroxybenzyl) sulfide, isooctyl 3,5-di-tert-butyl-4-hydroxybenzyl mercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis-(octylmercapto)-6-(3,5-ditert-butyl-4-hydroxyanilino)-s-triazine, octyl N-(3,5-di-tertbutyl-4-hydroxyphenyl)-carbamate.

1.7. Esters of β-(3,5-di-tert-butyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)-propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylene-diamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tertbutyl, 4'-octoxy, 3',5'-di-tert-amyl and 3',5'-bis(α,α-dimethylbenzyl) derivatives.

2.2. 2-Hydroxbenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tertbutyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methylα-cyano-β-methyl-p-methoxycinnamate, butyl α-cyanoβ-methyl-p-methoxycinnamate, methylα-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tertbutyl-4hydroxybenzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4piperidyl)hexamethylenediamine and 4-tert-octylamino-2,6-dichloro1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis(3,3,5,5-tetramethyl-piperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tertbutyloxanilide, 2-ethoxy-2'-ethyloxanilide, N,N'-bis(3-dimethylaminoprpyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and paramethoxy-disubstituted oxanilides and mixtures of o- and p-ethoxy-disubstituted oxanilides.

3. Metal deactivators, for example N,N'-diphenyl, N-salicylal-N'-salicyloylhydrazine, N,N'-bis(salicyloyl)-hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tertbutylphenyl) 4,4'-biphenylene-diphosphonite, 3,9-bis(2,4-di-tert-butylphenoxy)-2,4,8,10-tetra-oxa-3,9-diphosphaspiro[5.5]undecane.

5. Peroxide scavengers, for example esters of B-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, zinc stearate, magnesium stearate, sodium ricinoleate and potassium palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

Preferred compounds of formula (I) are those of Examples 1,2,4,9 and 14.

In the following examples the group

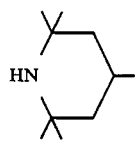

corresponds to 2,2,6,6-tetramethyl-4-piperidyl and the group

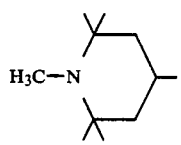

corresponds to 1,2,2,6,6-pentamethyl-4-piperidyl.

EXAMPLE 1

Preparation of

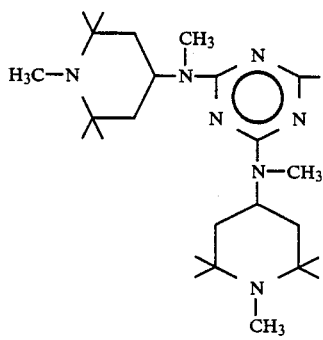

45.21 g (0.1 mol) of 2-chloro-4,6-bis[N-(2,6,6-tetramethyl-4-piperidyl-methylamino]-1,3,5-triazine and 5.16 g (0.05 mol) of diethylenetriamine in 200 ml of xylene are heated for 2 hours under reflux.

After the addition of 6.0 g (0.15 mol) of finely powdered sodium hydroxide, the mixture is heated for 14 hours under reflux, the water of reaction being simultaneously separated off azeotropically.

The mixture is cooled and washed with 3 times 80 ml of water. The organic solution thus obtained is heated to 110° C., and a solution consisting of 12.66 g (0.275 mol) of formic acid and 8.26 g (0.275 mol) of paraformaldehyde, previously dissolved in 15 ml of water containing 0.1 g of sodium hydroxide, is slowly added, the added water and the water of reaction being removed azeotropically.

After the end of the addition, the mixture is heated for 1 hour at 110° C. It is cooled to 80° C., and a solution of 4.0 g (0.1 mol) of sodium hydroxide in 20 ml of water is added. The mixture is heated for 1 hour under reflux and cooled to 80° C., and the aqueous phase is separated off. After washing with twice 80 ml of water, the organic solution is evaporated in vacuo (24 mbar), the product of melting point 167°-171° C. being obtained.

Analysis for $C_{55}H_{105}N_{17}$: Calculated $C=65.76\%$ $H=10.54\%$; $N=23.70\%$. Found: $C=65.12\%$; $H=10.39\%$; $N=23.68\%$.

EXAMPLES 2-4:

Proceeding analogously to Example 1 and using the respective intermediates and reagents in appropriate molar ratios, the products of the formula:

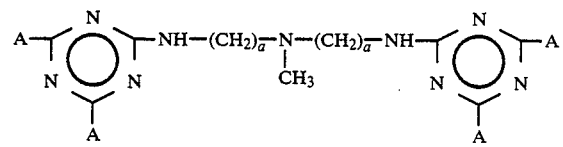

are obtained.

| Example | A | a | Melting point (°C.) |
|---|---|---|---|
| 2 | ![H3C-N piperidyl-N(C2H5)-] | 2 | 157–162 |
| 3 | ![H3C-N piperidyl-N(C2H5)-] | 3 | 118–122 |
| 4 | ![H3C-N piperidyl-N(C4H9(n))-] | 2 | 115–118 |

EXAMPLE 5

Preparation of

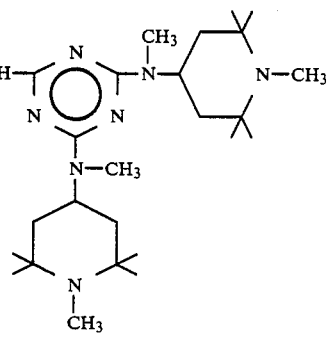

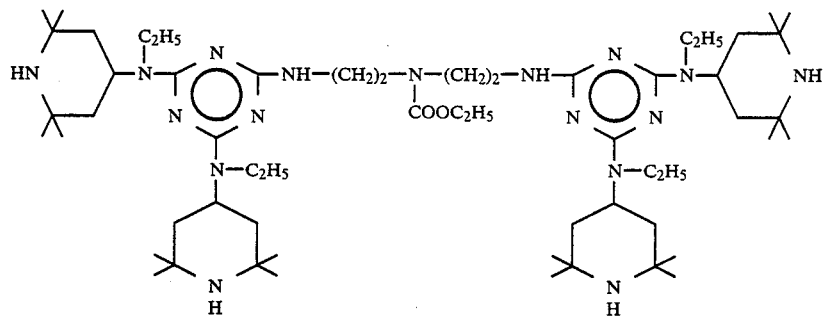

48.01 g (0.1 mol) of 2-chloro-4,6-bis[N-(2,2,6,6-tetramethyl-4-piperidyl)-ethylamino]-1,3,5-triazine and 5.16 g (0.05 mol) of diethylenetriamine in 200 ml of xylene are heated for 2 hours under reflux. After the addition of 6.0 g (0.15 mol) of finely powdered sodium hydroxide, the mixture is heated for a further 14 hours under reflux, the water of reaction being simultaneously separated off azeotropically. The mixture is cooled to ambient temperature and washed with 3 times 80 ml of water.

A solution of 5.43 g (0.05 mol) of ethyl chloroformate in 10 ml of xylene is then added to the organic solution cooled to −10° C.

After the end of the addition, the mixture is stirred for 2 hours at 0° C., and a solution of 2.0 g of sodium hydroxide in 20 ml of water is then slowly added. The mixture is then stirred for 1 hour at ambient temperature, and the aqueous phase is separated off. The solution is evaporated in vacuo (24 mbar); a product of melting point 115°–119° C. being obtained.

Analysis for $C_{57}H_{107}N_{17}O_2$: Calculated: C=64.42%; H=10.15%; N=22.41%. Found: C=64.37%; H=10.10%; N=22.35%.

EXAMPLES 6–17

Proceeding analogously to Example 5 and using the respective intermediates and reagents in appropriate molar ratios, the products of the formula:

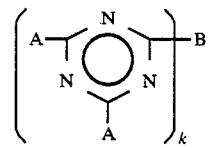

are obtained.

| Example | k | A | B | Melting point (°C.) |
|---|---|---|---|---|
| 6 | 2 | ![A group with CH3, HN, N-] | —NH—(CH$_2$)$_2$—N(COOC$_2$H$_5$)—(CH$_2$)$_2$—NH— | 129–133 |
| 7 | 2 | ![A group with C4H9(n), HN, N-] | —NH—(CH$_2$)$_2$—N(COOC$_2$H$_5$)—(CH$_2$)$_2$—NH— | 95–99 |
| 8 | 3 | ![A group with CH3, HN, N-] | —NH—(CH$_2$)$_3$—N—(CH$_2$)$_2$—N(COOC$_2$H$_5$)—(CH$_2$)$_3$—NH— | 134–138 |
| 9 | 3 | ![A group with C2H5, HN, N-] | —NH—(CH$_2$)$_3$—N—(CH$_2$)$_2$—N(COOC$_2$H$_5$)—(CH$_2$)$_3$—NH— | 127–131 |

-continued

| Example | k | A | B | Melting point (°C.) |
|---|---|---|---|---|
| 10 | 3 |  HN—[piperidine], N—C₄H₉(n) | —NH—(CH₂)₃—N(COOC₂H₅)—(CH₂)₂—N—(CH₂)₃—NH— | 92–95 |
| 11 | 4 | HN—[piperidine], N—C₂H₅ | —NH—(CH₂)₂—N—(CH₂)₂—NH—<br>COO(CH₂)₄OOC<br>—HN—(CH₂)₂—N—(CH₂)₂—NH— | 148–152 |
| 12 | 4 | HN—[piperidine], N—C₂H₅ | —NH—(CH₂)₃—N—(CH₂)₃—NH—<br>COO(CH₂)₄OOC<br>—HN—(CH₂)₃—N—(CH₂)₃—NH— | 141–145 |
| 13 | 4 | HN—[piperidine], N—C₄H₉(n) | —NH—(CH₂)₂—N—(CH₂)₂—NH—<br>COO(CH₂)₄OOC<br>—NH—(CH₂)₂—N—(CH₂)₂—NH— | 125–128 |
| 14 | 4 | HN—[piperidine], N—CH₃ | —NH—(CH₂)₃—N—(CH₂)₃—NH—<br>COO(CH₂)₄OOC<br>—NH—(CH₂)₃—N—(CH₂)₃—NH— | 145–149 |
| 15 | 6 | HN—[piperidine], N—CH₃ | —NH—(CH₂)₃—N—(CH₂)₂—N—(CH₂)₃—NH—<br>COO(CH₂)₄OOC<br>—NH—(CH₂)₃—N—(CH₂)₂—N—(CH₂)₃—NH— | 165–171 |
| 16 | 6 | HN—[piperidine], N—C₂H₅ | —NH—(CH₂)₃—N—(CH₂)₂—N—(CH₂)₃—NH—<br>COO(CH₂)₄OOC<br>—NH—(CH₂)₃—N—(CH₂)₂—N—(CH₂)₃—NH— | 142–145 |
| 17 | 6 | HN—[piperidine], N—C₄H₉(n) | —NH—(CH₂)₃—N—(CH₂)₂—N—(CH₂)₃—NH—<br>COO(CH₂)₄OOC<br>—NH—(CH₂)₃—N—(CH₂)₂—N—(CH₂)₃—NH— | 114–119 |

EXAMPLE 18

Preparation of

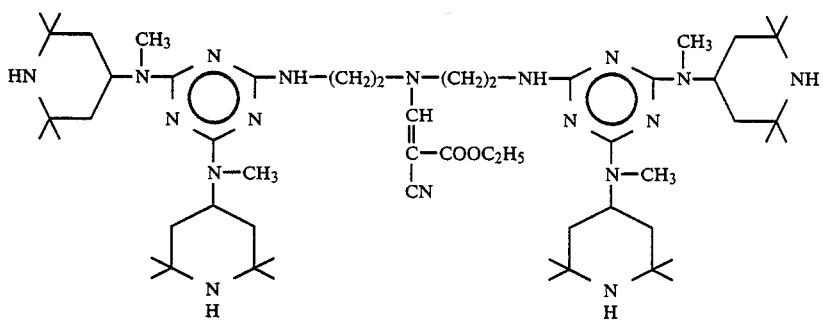

Proceeding analogously to Example 1, 45.21 g (0.1 mol) of 2-chloro-4,6bis[N-(2,2,6,6-tetramethyl-4-piperidyl)-methylamino]-1,3,5-triazine are reacted with 5.16 g (0.05 mol) of diethylenetriamine in 200 ml of xylene.

The organic solution of the condensation product is heated to 35°–40° C., and 8.46 g (0.05 mol) of ethyl (ethoxymethylene)-cyanoacetate are slowly added.

After the end of the addition, the mixture is heated for 5 hours at 60° C. and for another 4 hours at 80° C.

The solution is then evaporated in vacuo (24 mbar), a product of melting point = 140°–143° C. being obtained.

Analysis for $C_{56}H_{100}N_{18}O_2$: Calculated: C=63.60%; H=9.53%; N=23.84%. Found: C=63.18%; H=9.48%; N=23.68%.

EXAMPLE 19

Preparation of

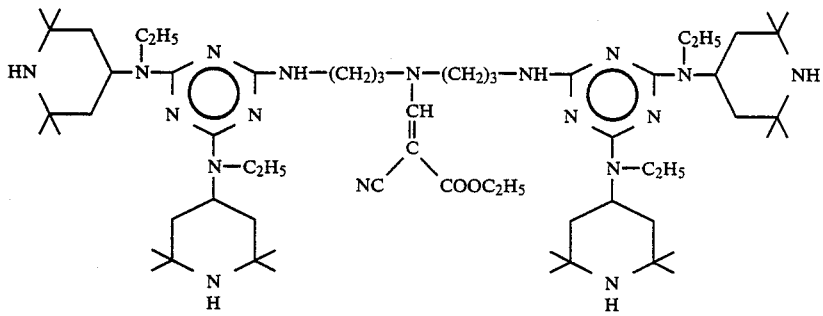

Proceeding analogously to Example 18, 45.84 g (0.045 mol) of the product obtained by condensation of 48.01 g (0.01 mol) of 2-chloro-4,6-bis[N(-2,2,6,6-tetramethyl-4-piperidyl)-ethylamino]-1,3,5-triazine with 6.56 g (0.05 mol) of dipropylenetriamine are reacted with 7.62 g (0.045 mol) of ethyl (ethoxymethylene)-cyanoacetate in 150 ml of xylene, a product of melting point 110°–114° C. being obtained.

Analysis for $C_{62}H_{112}N_{18}O_2$: Calculated: C=65.23%; H=9.89%; N=22.08%. Found: C=65.11%; H=9.82%; N=21.98%.

EXAMPLE 20

(Antioxidant action in polypropylene plaques)

1 g of each of the compounds indicated in Table 1 and 1 g of calcium stearate are mixed in a slow mixer with 1.000 g of polypropylene powder of melt index =2 g/10 minutes (measured at 230° C. and 2.16 kg).

The mixtures are extruded twice at 200°–220° C. to give polymer granules which are then converted into plaques of 1 mm thickness (mould according to DIN 53,451) by compression-moulding for 3 minutes at 220° C.

The plates obtained are exposed in a forced-circulation air oven maintained at a temperature of 135° C.

These specimens are periodically checked by bending through 180°, in order to determine the time (in hours) required for the onset of embrittlement.

Plates prepared under the same conditions as indicated above, but without the addition of the stabilizers, are exposed for comparison.

The results obtained are shown in table 1.

TABLE 1

| Stabilizer | Time to embrittlement (hours) |
|---|---|
| without stabilizer | 250 |
| compound from Example 1 | 1,360 |
| compound from Example 2 | 1,500 |
| compound from Example 4 | 1,350 |
| compound from Example 14 | 1,300 |
| compound from Example 18 | 1,440 |

EXAMPLE 21

(Light-stabilizing action in polypropylene fibres)

2.5 g of each of the products indicated in Table 2, 0.5 g of tris-(2,4-di-t-butylphenyl) phosphite, 0.5 g of calcium monoethyl 3,5-di-t-butyl-4hydroxybenzylphosphonate, 1 g of calcium stearate and 2.5 g of titanium dioxide (®KRONOS RN 57) are mixed in a slow mixer with 1,000 g of polypropyiene powder of melt index =12 g/10 minutes (measured at 230° C. and 2.16 kg).

The mixtures are extruded at 200°–220° C. to give polymer granules which are then converted into fibres, using a pilot-type apparatus (Leonard, Sumirago (VA), Italy) and operating under the following conditions:

extruder temperature: 200°–230° C.
head temperature: 255°–260° C.
stretch ratio: 1:3.5
denier: 11 dtex per filament The fibres thus produced are exposed, mounted on a white card, inamodel 65 WR Weather-O-Meter (ASTM G 26-77) at a black panel temperature of 63° C.

The residual tenacity is measured on samples, taken after various times of exposure to light, by means of a constant-speed tensometer; the exposure time in hours, needed to halve the initial tenacity is then calculated (T50).

Fibres prepared under the same conditions as indicated above, but without the addition of compounds according to the invention, are exposed for comparison.

The results obtained are shown in Table 2.

TABLE 2

| Stabilizer | T50 (hours) |
|---|---|
| without stabilizer | 150 |
| compound from Example 5 | 1,480 |
| compound from Example 8 | 1,460 |
| compound from Example 9 | 1,690 |
| compound from Example 10 | 1,330 |
| compound from Example 13 | 1,300 |
| compound from Example 14 | 1,700 |
| compound from Example 15 | 1,790 |
| compound from Example 16 | 1,690 |
| compound from Example 17 | 1,580 |
| compound from Example 19 | 1,460 |

EXAMPLE 22

(Light-stabilizing action in polypropylene tapes)

1 g of each of the compounds indicated in Table 3, 0.5 g of tris-(2,4-di-t-butylphenyl) phosphite, 0.5 g of pentaerythritol tetrakis-3-(3,5-di-t-butyl-4-hydroxyphenyl)-propionate and 1 g of calcium stearate are mixed in a slow mixer with 1,000 g of propylene powder of melt index =2 g /10 minutes (measured at 230° C. and 2.16 kg).

The mixtures are extruded at 200°-220° C. to give polymer granules which are then converted into stretched tapes of 50 um thickness and 2.5 mm width, using a pilot-type apparatus (Leonard-Sumirago (VA) Italy) and operating under the following conditions:
extruder temperature: 210°-230° C.
head temperature: 240°-260° C.
stretch ratio 1:6

The tapes thus prepared are exposed, mounted on a white card, in a model 65 WR Weather-O-Meter (ASTM G 26-77) at a black panel temperature of 63° C.

The residual tenacity is measured on samples, taken after various times of exposure to light, by means of a constant-speed tensometer; the exposure time (in hours) needed to halve the initial tenacity is then calculated (T50).

Tapes prepared under the same conditions as indicated above, but without the addition of stabilizer, are exposed for comparison.

The results obtained are shown in Table 3:

TABLE 3

| Stabilizer | T50 (hours) |
|---|---|
| without stabilizer | 500 |
| compound from Example 1 | 2,170 |
| compound from Example 2 | 2,200 |
| compound from Example 3 | 2,060 |
| compound from Example 4 | 2,300 |
| compound from Example 5 | 2,080 |
| compound from Example 6 | 2,030 |
| compound from Example 8 | 2,560 |
| compound from Example 9 | 2,770 |
| compound from Example 10 | 2,230 |
| compound from Example 14 | 2,500 |
| compound from Example 15 | 2,530 |

TABLE 3-continued

| Stabilizer | T50 (hours) |
|---|---|
| compound from Example 16 | 2,260 |
| compound from Example 19 | 2,240 |

What is claimed is:

1. A compound of the formula (I)

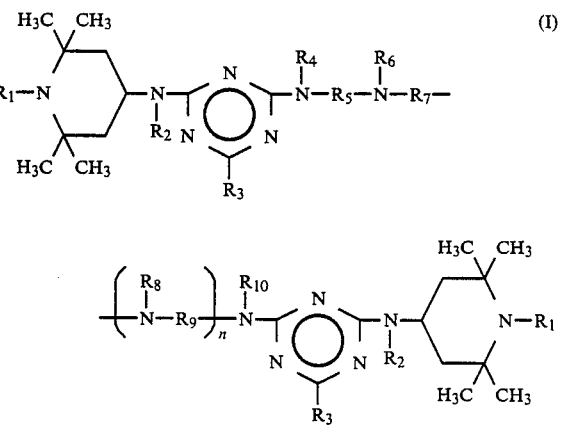

which $R_1$ is hydrogen, $C_1$-$C_4$alkyl, $O^*$, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono- di- or tri-substituted on the phenyl by $C_1$-$C_4$alkyl, $C_1$-$C_8$acyl or $C_2$-$C_4$alkyl substituted by one OH in the 2-, 3- or 4-position, $R_2$ is hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di-or tri-substituted on the phenyl by $C_1$-$C_4$alkyl, or $C_2$-$C_4$alkyl substituted by OH, $C_1$-$C_8$alkoxy or di-($C_1$-$C_4$alkyl)-amino in the 2-, 3- or 4-position, $R_3$ is $C_1$-$C_{18}$alkyl, phenyl which is unsubstituted or mono-, di- or tri-substituted by $C_1$-$C_4$alkyl, or one of the groups

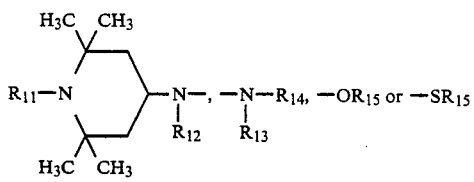

in which $R_{11}$ is as defined above for $R_1$, $R_{12}$ is as defined above for $R_2$, $R_{13}$ and $R_{14}$ which can be identical or different are as defined above for $R_2$ or are $C_3$-$C_6$alkenyl or, together with the nitrogen atom to which they are linked, form part of a 5-membered to 7-membered heterocyclic ring and $R_{15}$ is $C_1$-$C_{18}$alkyl, $C_5$-$C_{12}$cycloalkyl which is unsubstituted or mono-, di- or tri-substituted by $C_1$-$C_4$alkyl, $C_3$-$C_6$alkenyl, phenyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, of a group of the formula (II)

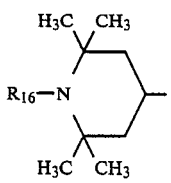
(II)

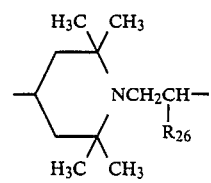

with R₁₆ being as defined above for R₁, R₄ and R₁₀ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl or a group of the formula (II), $R_5$, $R_7$ and $R_9$ which can be identical or different are $C_2$–$C_{12}$alkylene, n is zero or 1, $R_6$ and $R_8$ are $C_1$–$C_{18}$alkyl, $C_5$–$C_{12}$cycloalkyl which is unsubstituted or mono-, di- or tri-substituted by $C_1$–$C_4$alkyl, $C_3$–$C_6$alkenyl, $C_7$–$C_9$phenylalkyl which is unsubstituted or mono-, di- or tri-substituted on the phenyl by $C_1$–$C_4$alkyl, $C_2$–$C_4$alkyl substituted by OH in the 2-, 3-or 4-position, or a group of the formula (II) or $R_6$ and $R_8$ are one of the groups of the formula (IIIa)–(IIId)

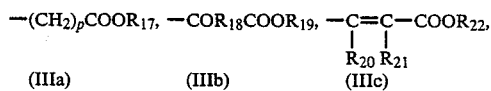

(IIIa)  (IIIb)  (IIIc)

—SO₂R₂₃

(IIId)

in which p is zero or an integer from 1 to 5, $R_{17}$, $R_{19}$ and $R_{22}$ which can be identical or different are $C_1$–$C_{18}$alkyl, $C_5$–$C_{12}$cycloalkyl which is unsubstituted or mono-, di- or tri-substituted by $C_1$–$C_4$alkyl, $C_3$–$C_{18}$alkenyl or a group of the formula (II), $R_{18}$ is a direct bond or $C_1$–$C_{12}$alkylene, cyclohexylene or phenylene, $R_{20}$ is hydrogen, $C_1$–$C_4$alkyl or phenyl, $R_{21}$ is —CN or a group —COOR₂₂ with $R_{22}$ being as defined above, and $R_{23}$ is $C_1$–$C_{18}$alkyl or phenyl which is unsubstituted or mono-, di- or tri-substituted by $C_1$–$C_4$alkyl, or $R_8$ is a group of the formula (IV)

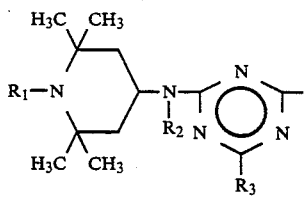
(IV)

with $R_1$, $R_2$ and $R_3$ being as defined above, and, if n is zero or if $R_8$ is a group of the formula (IV), $R_6$ can also be one of the groups of the formulae (Va) or (Vb)

—R₂₄X₁,    —COOR₂₅OOCX₁
(Va)          (Vb)

where $R_{24}$ is $C_2$–$C_{12}$alkylene, 2-hydroxytrimethylene or xylylene and $R_{25}$ is $C_2$–$C_{12}$alkylene, $C_4$–$C_{12}$alkylene interrupted by 1, 2 or 3 oxygen atoms, cyclohexylenedimethylene, methylenedicyclohexylene, isopropylidenedicyclohexylene, phenylene, xylylene or a group with R₂₆ being hydrogen, $C_1$–$C_4$alkyl or phenyl, and $X_1$ is a group of the formula (VI)

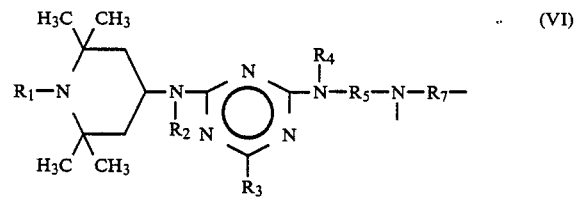
(VI)

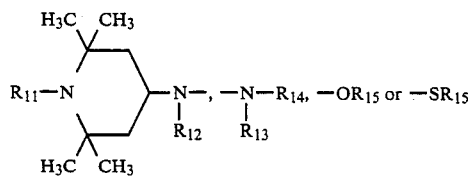

where $R_1$, $R_2$, $R_3$, $R_4$, $R_5$, $R_7$, $R_9$, $R_{10}$ and n are as defined above, and $X_2$ is a group of the formula (IV).

2. A compound of the formula (I) according to claim 1, in which $R_2$ is hydrogen, $C_1$–$C_{12}$alkyl, $C_5$–$C_8$cycloalkyl which is unsubstituted or mono-, di- or tri-substituted by $C_1$–$C_4$alkyl, benzyl or $C_2$–$C_3$alkyl substituted by OH, $C_1$–$C_4$alkoxy or di-($C_1$–$C_4$alkyl)-amino in the 2- or 3-position, $R_3$ is $C_1$–$C_{12}$alkyl, phenyl or one of the groups

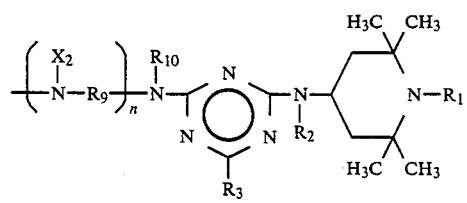

in which $R_1$ is as defined in claim 1 for $R_1$, $R_{12}$ is as defined above for $R_2$, $R_{13}$ and $R_{14}$ which can be identical or different are as defined above for $R_2$ or are allyl, or the group

—N—R₁₄
 |
 R₁₃ is 1-pyrrolidyl, 1-piperidyl, 4-morpholinyl or 1-hexahydroazepin-yl and $R_{15}$ is $C_1$–$C_{12}$alkyl, $C_5$–$C_8$cycloalkyl which is unsubstituted or mono-, di- or tri-substituted by $C_1$–$C_4$alkyl, allyl, phenyl, benzyl or a group of the formula (II) $R_4$ and $R_{10}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, or a group of the formula (II), $R_5$, $R_7$ and $R_9$ which can be identical or different are $C_2$–$C_{10}$-alkylene, n is zero or 1, $R_6$ and $R_8$ are $C_1$–$C_{12}$alkyl, $C_5$–$C_8$cycloalkyl which is unsubstituted or mono-, di- or tri-substituted by $C_1$ –$C_4$alkyl, allyl, benzyl, $C_2$–$C_3$alkyl substituted by OH in the 2- or 3-position, or a group of the formula (II) or $R_6$ and $R_8$ are one of the groups of the formulae (IIIa)–(IIId) in which p is zero or an integer from 1 to 3, $R_{17}$, $R_{19}$ and $R_{22}$ which can be identical or different are $C_1$–$C_{18}$alkyl, $C_5$–$C_8$cycloalkyl which is unsubstituted or mono-, di- or tri-substituted by $C_1$–$C_4$alkyl, $C_3$–$C_{18}$alkenyl or a group of the formula (II), $R_{18}$ is a direct bond or $C$–$C_{10}$alkylene, $R_{20}$ is hydrogen or $C_1$–$C_4$alkyl, $R_{21}$ is —CN or a group —COOR$_{22}$ with $R_{22}$ being as defined above and $R_{23}$ is $C_1$–$C_{12}$alkyl, phenyl or tolyl, or $R_8$ is a group of the formula (IV) and $R_6$ is also a group of the formula (Va) or (Vb) in which $R_{24}$ is $C_2$–$C_{10}$alkylene, 2-hydroxytrimethylene or xylylene, $R_{25}$ is $C_2$–$C_{10}$alkylene, $C_4$–$C_8$alkylene interrupted by 1, 2 or 3 oxygen atoms, cyclohexylenedimethylene, isopropylidenedicyclohexylene or a group

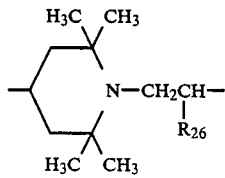

with $R_{26}$ being hydrogen or methyl, and $X_1$ is a group of the formula (VI).

3. A compound of the formula (I) according to claim 1, in which $R_2$ is hydrogen, $C_1$–$C_{12}$alkyl, cyclohexyl which is unsubstituted or mono-, di- or tri-substituted by $C_1$–$C_4$alkyl, benzyl or $C_2$–$C_3$alkyl substituted by OH, methoxy, ethoxy, dimethylamino or diethylamino in the 2- or 3-position, $R_3$ is $C_1$–$C_4$alkyl, phenyl or one of the groups

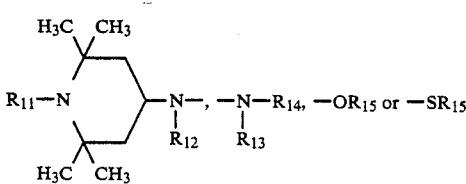

in which $R_{11}$ is as defined in claim 1, $R_{12}$ is as defined above for $R_2$, $R_{13}$ and $R_{14}$ which can be identical or different are as defined above for $R_2$ or are allyl, or the group

is 4-morpholinyl, and $R_{15}$ is $C_1$–$C_8$alkyl, cyclohexyl which is unsubstituted or mono-, di- or tri-substituted by $C_1$–$C_4$alkyl, allyl, phenyl, benzyl or a group of the formula (II(, $R_4$ and $R_{10}$ which can be identical or different are hydrogen, $C_1$–$C_8$alkyl, cyclohexyl or a group of the formula (II), $R_5$, $R_7$ and $R_9$ which can be identical or different are $C_2$–$C_8$alkylene, n is zero or 1, $R_6$ and $R_8$ are $C_1$–$C_8$alkyl, cyclohexyl which is unsubstituted or mono-, di- or tri-substituted by $C_1$–$C_4$alkyl, allyl, benzyl, 2-hydroxyethyl or one of the groups of the formulae (IIIa)–(IIId) in which p is zero or 1, $R_{17}$, $R_{19}$ and $R_{22}$ which can be identical or different are $C_1$–$C_{16}$alkyl, cyclohexyl which is unsubstituted or mono-, di- or trisubstituted by $C_1$–$C_4$alkyl, allyl, oleyl or a group of the formula (II), $R_{18}$ is a direct bond or $C_1$–$C_8$alkylene, $R_{20}$ is hydrogen or methyl, $R_{21}$ is —CN or a group —COOR$_{22}$ with $R_{22}$ being as defined above, and $R_{23}$ is $C_1$–$C_8$alkyl, phenyl or tolyl, or $R_8$ is a group of the formula (IV) and $R_6$ can also be a group of the formula (Va) or (Vb) in which $R_{24}$ is $C_2$–$C_8$alkylene, 2-hydroxytrimethylene or xylylene, $R_{25}$ is $C_2$–$C_8$alkylene, $C_4$–$C_6$alkylene interrupted by 1 or 2 oxygen atoms, cyclohexylenedimethylene, isopropylidenedicyclohexylene or a group

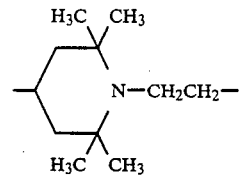

and $X_1$ is a group of the formula (VI).

4. A compound of the formula (I) according to claim 1, in which $R_2$ is hydrogen, $C_1$–$C_8$alkyl, cyclohexyl or $C_2$–$C_3$ alkyl which is substituted by OH, methoxy or ethoxy in the 2- or 3-position, $R_3$ is a group

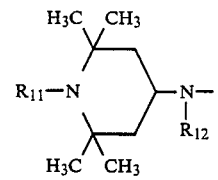

with $R_{11}$ being as defined above in claim 1 and $R_{12}$ being as defined above for $R_2$, $R_4$ and $R_{10}$ which can be identical or different are hydrogen, $C_1$–$C_4$alkyl, cyclohexyl or a group of formula (II), $R_5$, $R_7$ and $R_9$ which can be identical or different are $C_2$–$C_6$alkylene, n is zero or 1, $R_6$ and $R_8$ are $C_1$–$C_4$alkyl, allyl, benzyl or one of the groups of the formulae (IIIa)–(IIIc) in which p is zero, $R_{17}$, $R_{19}$ and $R_{22}$ which can be identical or different are $C_1$–$C_{12}$alkyl, cyclohexyl, t-butylcyclohexyl or a group of the formula (II), $R_{18}$ is a direct bond, $R_{20}$ is hydrogen and $R_{21}$ is —CN, or $R_8$ is a group of the formula (IV) and $R_6$ is also a group of the formula (Vb) in which $R_{25}$ is $C_4$–$C_8$alkylene, 3-oxapentane-1,5-diyl, cyclohexylenedimethylene or isopropylidenedicyclohexylene and $X_1$ is a group of the formula (VI).

5. A compound of the formula (I) according to claim 1, in which $R_1$ is hydrogen or methyl, $R_2$ is $C_1$–$C_8$alkyl, $R_3$ is a group

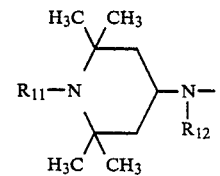

with $R_{11}$ being hydrogen or methyl and $R_{12}$ being $C_1$–$C_8$alkyl, $R_4$ and $R_{10}$ which can be identical or different are hydrogen or methyl, $R_5$, $R_7$ and $R_9$ which can be identical or different are -(CH$_2$)$_{2-3}$, n is zero or 1, $R_6$ and $R_8$ are methyl or a group —COOR$_{17}$ or

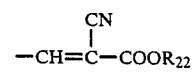

where $R_{17}$ and $R_{22}$ which can be identical or different are $C_1-C_8$alkyl, 2,2,6,6-tetramethyl-4-piperidyl or 1,2,2,6,6-pentamethyl-4-piperidyl, or $R_8$ is a group of the formula (IV) and $R_6$ is also a group $-COO(CH_2)_{4-6}OOCX_1$, where $X_1$ is a group of the formula (VI).

6. A compound of the formula (I) according to claim 1, in which $R_1$, $R_{11}$ and $R_{16}$ independently of one another are hydrogen, $C_1-C_4$alkyl, OH, $C_6-C_{12}$alkoxy, $C_5-C_8$cycloalkoxy, allyl, benzyl, acetyl or 2-hydroxyethyl.

7. A compound of the formula (I) according to claim 1, in which $R_1$, $R_{11}$ and $R_{16}$ independently of one another are hydrogen or methyl.

8. A compound of the formula (I) according to claim 1, in which $R_3$ is a group of the formula

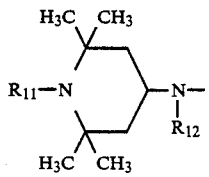

are which $R_{11}$ and $R_{12}$ are as defined above in claim 1, $R_4$ and $R_{10}$ independently of one another are hydrogen, $C_1-C_4$alkyl or a group of the formula (II), $R_6$ and $R_8$ independently of one another are $C_1-C_4$alkyl or a group of the formula (IIIa) or (IIIc), $R_8$ is additionally a group of the formula (IV) and $R_6$ is additionally a group of the formula (Vb).

9. A compound of the formula (I) according to claim 1, in which $R_3$ is a group of the formula

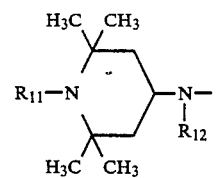

with $R_{11}$ and $R_{12}$ being as defined in claim 1.

10. The compound

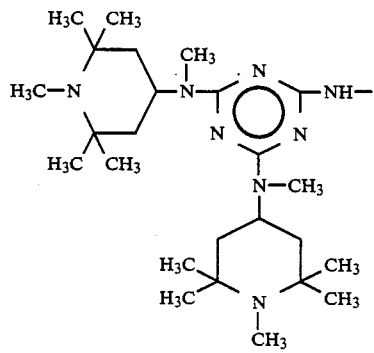
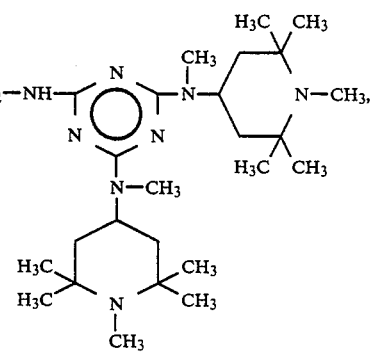
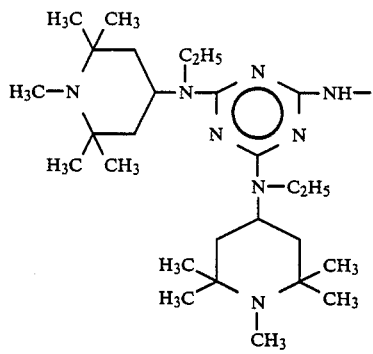
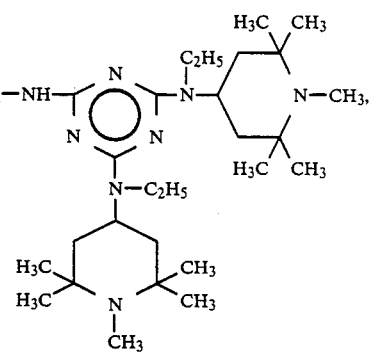
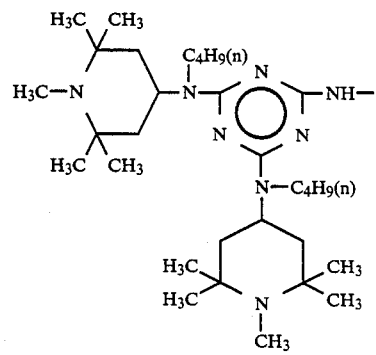
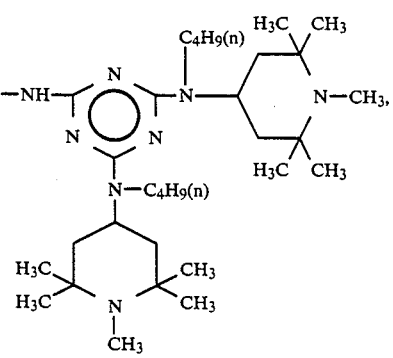

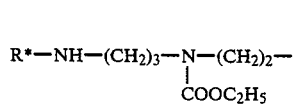 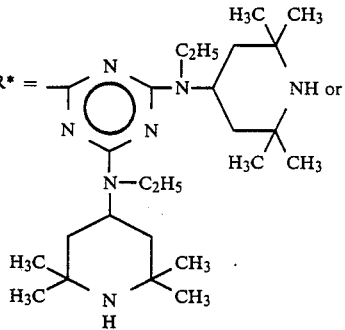
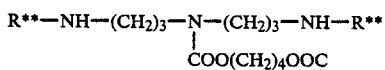
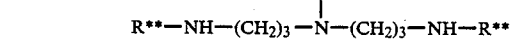
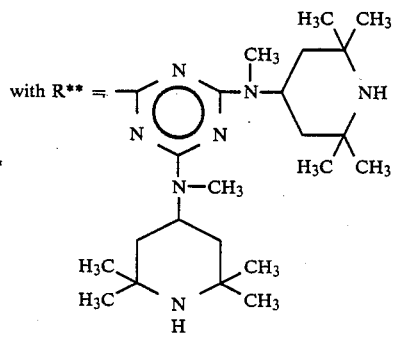
according to claim 1.